United States Patent
Goutsis

(10) Patent No.: US 10,226,412 B2
(45) Date of Patent: Mar. 12, 2019

(54) HAIR COLORING METHOD WITH LIQUID GLOVES

(71) Applicant: Henkel AG & Co. KGaA, Duesseldorf (DE)

(72) Inventor: Konstantin Goutsis, Juechen (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/435,139

(22) Filed: Feb. 16, 2017

(65) Prior Publication Data

US 2017/0239158 A1    Aug. 24, 2017

(30) Foreign Application Priority Data

Feb. 22, 2016   (DE) ........................ 10 2016 202 651

(51) Int. Cl.

| | |
|---|---|
| *A61Q 5/10* | (2006.01) |
| *A61K 8/46* | (2006.01) |
| *A45D 19/02* | (2006.01) |
| *A61K 8/04* | (2006.01) |
| *A61K 8/19* | (2006.01) |
| *A61K 8/24* | (2006.01) |
| *A61K 8/31* | (2006.01) |
| *A61K 8/34* | (2006.01) |
| *A61K 8/362* | (2006.01) |
| *A61K 8/365* | (2006.01) |
| *A61K 8/368* | (2006.01) |
| *A61K 8/37* | (2006.01) |
| *A61K 8/42* | (2006.01) |
| *A61K 8/44* | (2006.01) |
| *A61K 8/49* | (2006.01) |
| *A61K 8/60* | (2006.01) |
| *A61K 8/67* | (2006.01) |
| *A61K 8/73* | (2006.01) |
| *A61K 8/86* | (2006.01) |
| *A61K 8/92* | (2006.01) |
| *A61Q 5/02* | (2006.01) |
| *A61Q 19/00* | (2006.01) |
| *A61K 8/33* | (2006.01) |
| *A61Q 5/06* | (2006.01) |
| *A45D 19/00* | (2006.01) |

(52) U.S. Cl.
CPC .............. *A61K 8/463* (2013.01); *A45D 19/02* (2013.01); *A61K 8/046* (2013.01); *A61K 8/19* (2013.01); *A61K 8/24* (2013.01); *A61K 8/31* (2013.01); *A61K 8/33* (2013.01); *A61K 8/34* (2013.01); *A61K 8/345* (2013.01); *A61K 8/362* (2013.01); *A61K 8/365* (2013.01); *A61K 8/368* (2013.01); *A61K 8/375* (2013.01); *A61K 8/42* (2013.01); *A61K 8/44* (2013.01); *A61K 8/466* (2013.01); *A61K 8/498* (2013.01); *A61K 8/4926* (2013.01); *A61K 8/602* (2013.01); *A61K 8/673* (2013.01); *A61K 8/73* (2013.01); *A61K 8/731* (2013.01); *A61K 8/86* (2013.01); *A61K 8/922* (2013.01); *A61Q 5/02* (2013.01); *A61Q 5/065* (2013.01); *A61Q 5/10* (2013.01); *A61Q 19/00* (2013.01); *A45D 2019/0066* (2013.01); *A45D 2200/25* (2013.01); *A61K 2800/4324* (2013.01); *A61K 2800/596* (2013.01); *A61K 2800/5922* (2013.01); *A61K 2800/805* (2013.01); *A61K 2800/87* (2013.01); *A61K 2800/884* (2013.01)

(58) Field of Classification Search
CPC ............ A61Q 5/10; A61Q 5/19; A61K 8/466; A61K 8/375; A61K 8/34; A61K 8/731
See application file for complete search history.

(56) References Cited

U.S. PATENT DOCUMENTS

2015/0209250 A1*   7/2015   Massoni .................. A61K 8/22
                                                                                    8/406

\* cited by examiner

*Primary Examiner* — Eisa B Elhilo
(74) *Attorney, Agent, or Firm* — James J. Cummings

(57) ABSTRACT

A method for reducing skin staining during the coloring of hair includes the following steps in the indicated sequence:
- A1) applying a coloring agent (F) to the hair,
- A2) allowing the coloring agent (F) to act for a time period from 30 seconds to 45 minutes,
- B1) applying an undiluted cleaning agent (R) to skin areas that can come into contact with the coloring agent (F) when the latter is washed out,
- C1) jointly washing out the coloring agent (F) and cleaning agent (R), wherein
the coloring agent (F) includes at least one oxidation dye precursor and/or at least one direct dye and
the cleaning agent (R) includes at least one anionic surfactant.

A multicomponent packaging unit includes the coloring agent (F) and the cleaning agent (R).

13 Claims, No Drawings

HAIR COLORING METHOD WITH LIQUID GLOVES

FIELD OF THE INVENTION

The present invention generally relates to cosmetics, and more particularly relates to a method that enables coloring of hair with reduced skin staining.

The present invention also generally relates to a multi-component packaging unit (kit of parts), which comprises a suitable coloring agent and cleaning agent.

BACKGROUND OF THE INVENTION

The changing of the shape and color of hair is an important field in modern cosmetics. Because of this, the appearance of the hair can be adapted both to current fashion trends and to the individual wishes of the particular person. To change the hair color, the skilled artisan is familiar with a variety of coloring system depending on the coloring requirements. Oxidation dyes are typically used for permanent, intense dyeing with good fastness properties and good gray coverage. Such coloring agents typically include oxidation dye precursors, so-called developer components and coupler components, which together form the actual dyes under the influence of oxidizing agents, such as, for example, hydrogen peroxide. Oxidation dyes are notable for outstanding, long-lasting color results, but are also associated to a certain degree with hair damage.

If the user would like to change the hair color only temporarily, he/she can resort to coloring agents with direct dyes. In this case, already formed dyes diffuse from the coloring agent into the hair fiber. In comparison with oxidative hair coloring, the colors obtained with direct dyes have a lower durability and a more rapid washing out. Gray coverage, which can be achieved with direct dyes, are also generally in need of improvement. The reduced hair damage of coloring with direct dyes is advantageous, however.

There are various aids typically available to the user for applying these coloring agents.

The ready-to-use oxidative dyes are normally prepared shortly before use by mixing two components (color cream and formulation with oxidizing agents). The application mixture can be prepared in this case, for example, by combined shaking in a bottle, after which the application mixture is removed via a spout located on the bottle or an application aid. Optionally, the mixing of both components in a mixing bowl and the removal of the ready-to-use agent from the bowl using a brush or a dye brush are also possible.

Coloring agents based on direct dyes usually comprise only one component, which can be packaged, for example, in a tube or bottle. The application can occur in a similar way by direct removal from the bottle or also by transfer to a bowl.

Hair coloring agents were developed with the aim of coloring hair, i.e., keratinic material. Because the skin is a keratinic material as well, the dyes or oxidation dye precursors used in hair coloring agents also have the potential of staining the skin. This potential can be expressed more or less greatly depending on the dye class employed. In principle, direct dyes color the skin often more greatly than oxidation dye precursors, and in the case of acid dyes the skin staining is often especially pronounced.

To minimize skin staining, it is therefore advantageous to prevent any skin contact with the coloring agents whenever possible. There are different aids available to the user for the accurate application of the coloring agent such as, for example, the previously described applicators or spouts. When the coloring agent is applied, the hands or the forehead area of the user need not necessarily come into contact with the coloring agent.

The coloring agent must be rinsed out as completely and thoroughly as possible, however. The user generally must usually use his/her hands for this process. The forehead or nape area also invariably comes into contact with the coloring agent during the washing out process.

In order to minimize contact between hands and coloring agents when the coloring agent is rinsed out, a coloring product usually also includes a pair of gloves that the user can wear during the rinsing out process.

Providing gloves is typical practice in products intended for single use. If, in contrast, the amount included in the coloring product is designed for multiple use, providing several pairs of gloves is neither an economically viable nor a lasting solution.

Lastly, there are also application forms that make the wearing of gloves impractical during single use as well. To cover only slightly gray hair, individual gray hair areas, or the roots, there are products on the market, for example, that require only a short contact time and can also be used in the shower. Wearing gloves in the shower also does not appear to be very convenient for the user.

It is therefore desirable to provide a method for the above-described application forms, a method that enables the coloring of hair with the minimization of skin staining, without the user being instructed to use gloves while washing out the agent.

Furthermore, other desirable features and characteristics of the present invention will become apparent from the subsequent detailed description of the invention and the appended claims, taken in conjunction with this background of the invention.

BRIEF SUMMARY OF THE INVENTION

A method for reducing skin staining during the coloring of hair includes the following steps in the indicated sequence: applying a coloring agent (F) to the hair, allowing the coloring agent (F) to act for a time period from 30 seconds to 45 minutes, applying an undiluted cleaning agent (R) to skin areas that can come into contact with the coloring agent (F) when the latter is washed out, and jointly washing out the coloring agent (F) and cleaning agent (R). The coloring agent (F) includes at least one oxidation dye precursor and/or at least one direct dye, and the cleaning agent (R) includes at least one anionic surfactant.

A multicomponent packaging unit (kit of parts) for coloring hair with reduced skin staining includes, packaged separately from one another, an aqueous coloring agent (F), and an aqueous cleaning agent (R). The coloring agent (F) includes at least one oxidation dye precursor and/or at least one direct dye, and the cleaning agent (R) includes at least one anionic surfactant. The pH of the cleaning agent (R) differs by at least 1.5 pH units, preferably by at least 2.0 pH units, more preferably by at least 3.0 pH units, and very particularly preferably by at least 4.0 pH units from the pH of the coloring agent (F).

DETAILED DESCRIPTION OF THE INVENTION

The following detailed description of the invention is merely exemplary in nature and is not intended to limit the invention or the application and uses of the invention.

Furthermore, there is no intention to be bound by any theory presented in the preceding background of the invention or the following detailed description of the invention.

In the work leading to this invention, it has now been found that surfactant-containing cleaning agents can prevent skin staining to a significant extent, when they are distributed on all hair areas before the coloring agent is rinsed out, areas that can come into contact with the coloring agent during the later rinsing out process.

A first subject of the present invention is a method for reducing skin staining during the coloring of hair, comprising the following steps in the indicated sequence:

A1) applying a coloring agent (F) to the hair,
A2) allowing the coloring agent (F) to act for a time period from 30 seconds to 45 minutes,
B1) applying an undiluted cleaning agent (R) to skin areas that can come into contact with the coloring agent (F) when the latter is washed out,
C1) jointly washing out the coloring agent (F) and cleaning agent (R),
wherein
the coloring agent (F) includes at least one oxidation dye precursor and/or at least one direct dye and
the cleaning agent (R) includes at least one anionic surfactant.

The first subject of the invention is a method for reducing skin staining during the coloring of hair. It is meant hereby that hair can be dyed by the method, wherein skin areas, which are usually also dyed during the coloring process in an undesirable manner, are stained less or not at all in comparison with a method that is not of the invention.

The method of the invention is characterized by the sequence of steps A1), followed by A2), followed by B1), followed by C1).

First, a coloring agent (F) is applied to the hair in step A1). The coloring agent is characterized by its content of at least one oxidation dye precursor and/or at least one direct dye.

The coloring agent (F) in step A1) can be applied in fact in principle by the hands as well. This variant is explicitly not preferred, because the method of the invention is to enable the nonuse of gloves and in this process step the hands are not yet protected by the "liquid gloves."

Preferred is the application of the coloring agent (F) with all application aids that allow application without contact between the (not gloved) hands and the coloring agent (F). For example, a comb, an applicator, a dye brush, a spout, or a brush can serve as application aids.

In one embodiment, a method of the invention is very particularly preferred that comprises
A1) applying a coloring agent (F) to the hair using a comb, an applicator, a dye brush, a spout, or a brush.

An applicator can be, for example, a device which is provided with tines or also with a small sponge, is located either separately on a handle or, however, has an outlet opening and can be screwed onto the bottle, containing the ready-to-use coloring agent (F). A dye brush is a special type of a wide, thin brush, located on a rather long handle. A spout is, for example, an outlet opening, located on the bottle containing the ready-to-use coloring agent (F).

After application, the coloring agent (F) in step A2) is allowed to act on the hair for a time period of 30 seconds to 45 minutes.

The contact time depends both on the dye concentration in the agent and also on the product concept. Thus, a full head coloring, in which an intense and uniform color result is desired, is allowed to act on the hair preferably for a longer time period, whereas a rapid root coloring, a coloring to cover slightly gray hair, or a partial coloring of specific hair areas can also be rinsed out again after shorter contact times.

The method of the invention is particularly suitable for coloring processes with shorter contact times, which can be carried out, for example, during the morning routine, without much effort and then can also be rinsed out again rapidly, for example, in the shower.

In one embodiment, a method of the invention is very particularly preferred that comprises
A2) allowing the coloring agent (F) to act for a time period of 30 seconds to 15 minutes, preferably of 30 seconds to 10 minutes, particularly preferably of 30 seconds to 5 minutes.

After the coloring agent contact time has elapsed, then in step B1) an undiluted cleaning agent is applied to skin areas that could come into contact with the coloring agent when it is washed out.

According to the invention, therefore, explicitly no wash-out process takes place between steps A2) and B1). In other words, in the method of the invention after the contact time defined in step A2) has elapsed, in step B1) a cleaning agent is removed from the product package and applied in undiluted form, i.e., without use of water, to one or more skin areas that can come into contact with the coloring agent when it is washed out and can then be stained as a result.

These skin regions are, for example, the hands and all visible areas of the head region such as, for example, the forehead and temporal region, the ears, nape, and skin areas adjacent to the hairline, such as, for example, the side and back areas of the neck.

The scalp can also be stained by the use of the coloring agent (F), but the scalp stains are concealed by the hair covering the scalp and are generally perceived as less objectionable by the user.

In step B1), the user need not necessarily cover all of the aforementioned skin areas with the cleaning agent (R), but can also select individually the regions where he or she perceives skin staining as especially objectionable.

The feature of the undiluted cleaning agent (R) is taken to mean according to the invention that the cleaning agent is not to be mixed with water before or during the application in step B1) but is removed directly from the container, in which it was provided to the user, and is applied to skin regions in this form.

The application of the cleaning agent (R) to the hands can occur, for example, by removing and subsequent rubbing in of a portion from the product package. The application to the forehead, nape, and/or ears can occur, for example, directly with the hands or also with use of a small sponge, brush, applicator, or cloth.

In one embodiment, a method of the invention is very particularly preferred that comprises
B1) applying an undiluted cleaning agent (R) to the hands, ears, nape, forehead area, and/or skin areas adjacent to the hairline.

The use of the invention of the cleaning agent (R) forms a protective or barrier layer on all skin areas to which the cleaning agent (R) was applied; said layer minimizes the contact between the skin and coloring agent (F) and prevents the diffusion of the dyes through the layer.

After step B1), the joint washing out of the coloring agent (F) and of the cleaning agent (R) then takes place in step C1).

"Joint" is also understood to be synonymous with "concurrent"; i.e., both the coloring agent (F) and the cleaning agent (R) are on the user's body areas and are washed out in a joint washing out process with water.

In other words, the subject of the present invention is a method for reducing skin staining during the coloring of hair, comprising the following steps in the indicated sequence:

A1) applying a coloring agent (F) to the hair,
A2) allowing the coloring agent (F) to act for a time period from 30 seconds to 45 minutes,
B1) applying an undiluted cleaning agent (R) to skin areas that can come into contact with the coloring agent (F) when the latter is washed out,
C1) concurrently washing out the coloring agent (F) and cleaning agent (R),
wherein
the coloring agent (F) includes at least one oxidation dye precursor and/or at least one direct dye and
the cleaning agent (R) includes at least one anionic surfactant.

For step C1), the user very particularly preferably uses his/her hands that are not protected by gloves. The cleaning agent (R) on the hands minimizes or prevents skin staining. Moreover, the surfactants included in the cleaning agent (R) bring about an emulsification of the dyes, as a result of which both the staining is reduced and the washing out of the dyes is facilitated.

In one embodiment, a method of the invention is very particularly preferred, comprising
C1) jointly (i.e., concurrently) washing out the coloring agent (F) and cleaning agent (R) without the use of gloves.

The coloring agent (F) is designed for coloring hair, and therefore it includes at least one oxidation dye precursor and/or at least one direct dye.

The group of oxidation dye precursors is divided into compounds of the developer type and compounds of the coupler type. Particularly suitable oxidation dye precursors of the developer type in the present case are selected from at least one compound from the group formed by p-phenylenediamine, p-toluylenediamine, 2-(2-hydroxyethyl)-p-phenylenediamine, dihydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis(2-hydroxyethyl)-N,N'-bis(4-aminophenyl)-1,3-diaminopropan-2-ol, bis(2-hydroxy-5-aminophenyl)methane, 1,3-bis(2,5-diaminophenoxy)propan-2-ol, N,N'-bis(4-aminophenyl)-1,4-diazacyclo-heptane, 1,10-bis(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo [1,2-a]pyrazol-1-one, and the physiologically acceptable salts thereof.

Especially suitable oxidation dye precursors of the coupler type in the present case are selected from the group formed by 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy) propane, 1-methoxy-2-amino-4-(2-hydroxyethyl-amino) benzene, 1,3-bis(2,4-diaminophenyl)propane, 2,6-bis(2'-hydroxyethyl)-1-methylbenzene, 2-({3-[(2-hydroxyethyl) amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl) amino]-4,5-dimethylphenyl}-amino)ethanol, 2-[3-morpholin-4-ylphenyl)amino]ethanol, 3-amino-4-(2-methoxy-ethoxy)-5-methylphenylamine, 1-amino-3-bis(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of said compounds or the physiologically acceptable salts thereof.

The oxidation dye precursors of the developer type and of the coupler type can be used, for example, based on the total weight of the coloring agent (F), in a total amount of 0.0001 to 7.0% by weight, preferably 0.001 to 3.5% by weight. In this case, developer components and coupler components are generally used in approximately molar amounts to one another. Although molar use has proven to be expedient, a certain excess of individual oxidation dye precursors is not disadvantageous, so that developer components and coupler components may have a molar ratio of 1 to 0.5 to 1 to 3, particularly 1 to 1 to 1 to 2.

If the coloring agent of the invention includes oxidation dye precursors of the developer and/or coupler type, thus coloring agent (F) is the ready-to-use coloring agent, which is prepared shortly before use by mixing a first preparation that includes the oxidation dye precursors of the developer and coupler type, with a second preparation that includes an oxidizing agent.

In a b embodiment, the coloring agent (F) therefore can include in addition at least one oxidizing agent. A particularly preferred oxidizing agent is hydrogen peroxide. In a preferred embodiment, hydrogen peroxide itself is used as an aqueous solution. The concentration of a hydrogen peroxide solution in the coloring agent (F) of the invention is determined, on the one hand, by legal requirements and, on the other, by the desired effect; preferably, 6 to 12% by weight solutions in water are used. Coloring agents (F) preferred according to the invention are characterized in that they include, based on the total weight of the coloring agent (F), 0.5 to 20% by weight, preferably 1 to 12.5% by weight, particularly preferably 2.5 to 10% by weight, and in particular 3 to 6% by weight of hydrogen peroxide.

In a further embodiment, a coloring agent (F) of the invention is characterized in that it includes, based on the total weight of the agent, 0.5 to 12.5% by weight, preferably 2.5 to 10% by weight, and in particular 3 to 6% by weight of hydrogen peroxide.

Particularly preferably, the coloring agent (F) includes at least one direct dye. Direct dyes (a) can be divided into anionic, cationic, and nonionic direct dyes. The direct dyes are preferably selected from nitrophenylenediamines, nitroaminophenols, azo dyes, anthraquinones, triarylmethane dyes, or indophenols, and the physiologically acceptable salts thereof.

Dyes that carry exclusively cationic charges are typically also called basic dyes. The skilled artisan uses the term 'acid dyes' in the case of dyes that carry exclusively anionic charges.

In a further embodiment, very particularly preferred is a method for reducing skin staining during the coloring of hair, comprising the following steps in the indicated sequence:

A1) applying a coloring agent (F) to the hair,
A2) allowing the coloring agent (F) to act for a time period from 30 seconds to 45 minutes,
B1) applying an undiluted cleaning agent (R) to skin areas that can come into contact with the coloring agent (F) when the latter is washed out,
C1) jointly (i.e., concurrently) washing out the coloring agent (F) and cleaning agent (R),
wherein
the coloring agent (F) includes at least one cationic and/or anionic direct dye and
the cleaning agent (R) includes at least one anionic surfactant.

The direct dye(s) can be included preferably in a total amount of 0.01 to 5.5% by weight, preferably of 0.08 to 4.7% by weight, more preferably of 0.2 to 3.4% by weight, and particularly preferably of 0.3 to 1.8% by weight in the coloring agent (F). The calculation basis for the total amount of the direct dyes in this case is the total weight of the coloring agent (F).

When anionic dyes (acid dyes) are used, the skin can be stained especially greatly. When acid dyes are used, protecting the skin before the staining is therefore very particularly important.

The terms 'anionic dye' and 'acid dye' are used synonymously in the context of the present invention. Anionic dyes or acid dyes are understood to be direct dyes that have at least one carboxylic acid group (—COOH) and/or a sulfonic acid group (—SO$_3$H). Depending on the pH, the protonated forms (—COOH, —SO$_3$H) of carboxylic acid or sulfonic acid groups are present in equilibrium with their deprotonated forms (—COO$^-$, —SO$_3^-$). The proportion of the protonated forms increases with a decreasing pH. If direct dyes are used in the form of their salts, thus the carboxylic acid groups or sulfonic acid groups are present in the deprotonated form and are neutralized to maintain the electroneutrality with corresponding stoichiometric equivalents of cations (such as, for example, Na cations or K cations). An anionic dyes carries no cationic charges.

For example, one or more compounds can be selected as suitable acid dyes from the following group: Acid Yellow 1 (D&C Yellow 7, Citronin A, Ext. D&C Yellow No. 7, Japan Yellow 403, CI 10316, COLIPA no B001), Acid Yellow 3 (COLIPA no: C 54, D&C Yellow No 10, Quinoline Yellow, E104, Food Yellow 13), Acid Yellow 9 (CI 13015), Acid Yellow 17 (CI 18965), Acid Yellow 23 (COLIPA no C 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA no C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodiumsalt; Brown No. 201; RESORCIN BROWN; ACID ORANGE 24; Japan Brown 201; D & C Brown No. 1), Acid Red 14 (C.I. 14720), Acid Red 18 (E124, Red 18; CI 16255), Acid Red 27 (E 123, CI 16185, C-Rot 46, Echtrot D, FD&C Red Nr. 2, Food Red 9, Naphtholrot S), Acid Red 33 (Red 33, Fuchsia Red, D&C Red 33, CI 17200), Acid Red 35 (CI 18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red no 106, Pontacyl Brilliant Pink), Acid Red 73 (CI 27290), Acid Red 87 (Eosin, CI 45380), Acid Red 95 (CI 45425, Erythrosine, Simacid Erythrosine Y), Acid Red 184 (CI 15685), Acid Red 195, Acid Violet 43 (Jarocol Violet 43, Ext. D&C Violet no 2, C.I. 60730, COLIPA no C063), Acid Violet 49 (CI 42640), Acid Violet 50 (CI 50325), Acid Blue 1 (Patent Blue, CI 42045), Acid Blue 3 (Patent Blau V, CI 42051), Acid Blue 7 (CI 42080), Acid Blue 104 (CI 42735), Acid Blue 9 (E 133, Patentblau AE, Amidoblau AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I. 42100), Acid Green 22 (C.I. 42170), Acid Green 25 (CI 61570, Japan Green 201, D&C Green No. 5), Acid Green 50 (Brillantsäuregrün BS, C.I. 44090, Acid Brilliant Green BS, E 142), Acid Black 1 (Black no 401, Naphthalene Black 10B, Amido Black 10B, CI 20 470, COLIPA no B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2, and/or D&C Brown 1.

In a further embodiment, very particularly preferred is a method for reducing skin staining during the coloring of hair, comprising the following steps in the indicated sequence:
A1) applying a coloring agent (F) to the hair,
A2) allowing the coloring agent (F) to act for a time period from 30 seconds to 45 minutes,
B1) applying an undiluted cleaning agent (R) to skin areas that can come into contact with the coloring agent (F) when the latter is washed out,
C1) jointly (i.e., concurrently) washing out the coloring agent (F) and cleaning agent (R),
wherein
the coloring agent (F) includes at least one anionic direct dye from the group comprising Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 18, Acid Red 27, Acid Red 33, Acid Red 35, Acid Red 51, Acid Red 52, Acid Red 73, Acid Red 87, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 7, D&C Yellow 8, D&C Orange 4, D&C Green 5, D&C Orange 10, D&C Orange 11, D&C Red 21, D&C Red 27, D&C Red 33, D&C Violet 2, and D&C Brown 1, and
the cleaning agent (R) includes at least one anionic surfactant.

The coloring agent (F) can include the acid dye(s) preferably in a total amount of 0.01 to 5.5% by weight, preferably of 0.08 to 4.7% by weight, more preferably of 0.2 to 3.4% by weight, and particularly preferably of 0.3 to 1.8% by weight. The calculation basis for the total amount of the acid dyes in this case is the total weight of the coloring agent (F).

The cleaning agent (R) is applied to the skin before the washing out of the coloring agent (F); it should form a protective film, emulsify the dyes (or oxidation dye precursors) during the later washing out, and prevent the penetration thereof into the skin. It emerged that these effects can be achieved by the use of at least one anionic surfactant in the cleaning agent (R).

Surfactants are amphiphilic (bifunctional) compounds that consist of at least one hydrophobic and at least one hydrophilic moiety. The hydrophobic group is preferably a hydrocarbon chain having 8-24 carbon atoms, which may be saturated or unsaturated, linear or branched. Particularly preferably, this C8-C24 alkyl chain is linear.

In the case of anionic surfactants, the hydrophilic moiety comprises a negatively charged hydrophilic head group. The negatively charged hydrophilic head group can be, for example, a carboxylic acid group or the salt of a carboxylic acid group, a sulfonic acid group or the salt of the sulfonic acid group, a sulfonic acid ester group or the salt thereof, a phosphonic acid group or the salt of the phosphonic acid group, or a phosphoric acid ester group or the salt thereof.

The cleaning agent (R) of the invention typically comprises an aqueous carrier. The aforementioned hydrophilic head groups of the anionic surfactant, such as, for example, carboxylic acid and the salts of carboxylic acids, are present in the aqueous solution in an equilibrium, whose position is codetermined by the pH of the agent. If, for example, a fatty acid is used as an anionic surfactant, thus a smaller part of the fatty acid is present in the aqueous solution in the form of the protonated fatty acid, whereas the major part of the fatty acid is deprotonated in the aqueous solution and is converted in this way to the salt of the fatty acid. For this reason, the definition of an anionic surfactant also comprises a surfactant with a, not yet protonated, acid group.

An anionic surfactant in the context of the present invention includes no cationic groups; i.e., zwitterionic surfactants are not included in the definition of an anionic surfactant.

Anionic surfactants of the invention are accordingly characterized by the presence of an anionic group imparting water solubility, such as, e.g., a carboxylate, sulfate, sulfonate, or phosphate group, and a lipophilic alkyl group having approximately 8 to 30 C atoms. In addition, glycol ether or polyglycol ether groups, ester, ether, and amide groups, and hydroxyl groups can be included in the molecule.

Typical examples of anionic surfactants are alkylbenzene sulfonates, alkane sulfonates, olefin sulfonates, alkyl ether sulfonates, glycerol ether sulfonates, α-methyl ester sulfonates, sulfo fatty acids, alkyl sulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, acyl lactylates, acyl tartrates, acyl glutamates, acyl aspartates, alkyl oligoglucoside sulfates, protein fatty acid condensates (particularly plant products with a wheat base), and alkyl (ether) phosphates. Provided the anionic surfactants include polyglycol ether chains, these can have a conventional but preferably narrow homolog distribution.

Examples of anionic surfactants of the invention are, each in the form of the sodium, potassium, and ammonium and mono-, di-, and trialkanolammonium salts having 2 to 4 C atoms in the alkanol group, linear and branched fatty acids having 8 to 30 C atoms (soaps),
ether carboxylic acids of the formula R—O—($CH_2$—$CH_2O)_x$—$CH_2$—COOH, in which R is a linear alkyl group having 8 to 30 C atoms and x=0 or is 1 to 16,
acyl sarcosides having 8 to 24 C atoms in the acyl group,
acyl taurides having 8 to 24 C atoms in the acyl group,
acyl isethionates, having 8 to 24 C atoms in the acyl group, which are obtained by esterification of fatty acids with the sodium salt of 2-hydroxyethanesulfonic acid (isethionic acid). If fatty acids having 8 to 24 C atoms, therefore, e.g., lauric, myristic, palmitic, or stearic acid or technical fatty acid fractions as well, e.g., the $C_{12}$-$C_{18}$ fatty acid fraction, obtainable from coconut fatty acid, are used for this esterification, $C_{12}$-$C_{18}$ acyl isethionates preferably suitable according to the invention are obtained,
sulfosuccinic acid mono- and dialkyl esters having 8 to 24 C atoms in the alkyl group, and sulfosuccinic acid monoalkylpolyoxyethyl esters having 8 to 24 C atoms in the alkyl group and 1 to 6 oxyethyl groups. Sulfosuccinic acid mono- and dialkyl esters can be prepared by reacting maleic anhydride with a fatty alcohol having 8-24 C atoms to form maleic acid monoesters of the fatty alcohol and further reaction with sodium sulfite to form sulfosuccinic acid esters. Especially suitable sulfosuccinic acid esters are derived from fatty alcohol fractions having 12 to 18 C atoms, as they can be obtained, e.g., from coconut fatty acid or coconut fatty acid methyl esters by hydrogenation,
linear alkane sulfonates having 8 to 24 C atoms,
linear alpha-olefin sulfonates having 8 to 24 C atoms,
alpha-sulfo fatty acid methyl esters of fatty acids having 8 to 30 C atoms,
alkyl sulfates and alkyl polyglycol ether sulfates of the formula R—O($CH_2$—$CH_2O)_x$—$OSO_3H$, in which R is a preferably linear alkyl group having 8 to 30 C atoms and x=0 or is 1 to 12,
hydroxysulfonates substantially corresponding to at least one of the two following formulas or mixtures thereof and salts thereof, $CH_3$—$(CH_2)_y$—CHOH—$(CH_2)_p$—(CH—$SO_3M$)-$(CH_2)_z$—$CH_2$—O—$(C_nH_{2n}O)_x$—H, and/or $CH_3$—$(CH_2)_y$—(CH—$SO_3M$)-$(CH_2)_p$—CHOH—$(CH_2)_z$—$CH_2$—O—$(C_nH_{2n}O)_x$—H wherein in both formulas y and z=0 or integers from 1 to 18, p=0, 1, or 2 and the sum (y+z+p) is a number from 12 to 18, x=0 or is a number from 1 to 30 and n is an integer from 2 to 4 and M=H or alkali, particularly sodium, potassium, lithium, alkaline earth, particularly magnesium, calcium, zinc, and/or an ammonium ion, which optionally may be substituted, particularly mono-, di-, tri-, or tetraammonium ions having C1 to C4 alkyl, alkenyl, or aryl groups,
sulfated hydroxyalkyl polyethylene and/or hydroxyalkylene propylene glycol ethers, of the formula $R^1$—(CHOSO$_3$M)-CHR$_3$—(OCHR$^4$—CH$_2)_n$—OR$^2$ in which $R^1$ stands for a linear alkyl group having 1 to 24 C atoms, $R^2$ for a linear or branched, saturated alkyl group having 1 to 24 C atoms, $R^3$ for hydrogen or a linear alkyl group having 1 to 24 C atoms, $R^4$ for hydrogen or a methyl group, and M for hydrogen, ammonium, alkylammonium, alkanolammonium, where the alkyl and alkanol groups each have 1 to 4 C atoms, or a metal atom selected from lithium, sodium, potassium, calcium, or magnesium, and n for a number in the range of 0 to 12, and furthermore the total number of C atoms in $R^1$ and $R^3$ is 2 to 44,
sulfonates of unsaturated fatty acids having 8 to 24 C atoms and 1 to 6 double bonds,
esters of tartaric acid and citric acid with alcohols, representing adducts of approximately 2 to 15 molecules of ethylene oxide and/or propylene oxide to fatty alcohols having 8 to 22 C atoms, alkyl and/or alkenyl ether phosphates of the formula,

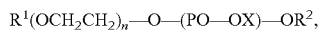

in which $R^1$ preferably stands for an aliphatic hydrocarbon group having 8 to 30 carbon atoms, $R^2$ for hydrogen, a group $(CH_2CH_2O)_nR^2$, or X, n for numbers from 1 to 10, and X for hydrogen, an alkali metal or alkaline earth metal or $NR^3R^4R^5R^6$, where $R^3$ to $R^6$ independently of one another stand for hydrogen or a $C_1$ to $C_4$ hydrocarbon group, sulfated fatty acid alkylene glycol esters of the formula $RCO(AlkO)_nSO_3M$ in which RCO— stands for a linear or branched, aliphatic, saturated and/or unsaturated acyl group having 6 to 22 C atoms, Alk for $CH_2CH_2$, $CHCH_3CH_2$, and/or $CH_2CHCH_3$, n for numbers from 0.5 to 5, and M for a metal, such as an alkali metal, particularly sodium, potassium, lithium, alkaline earth metal, particularly magnesium, calcium, zinc, or ammonium ion, such as $^+NR^3R^4R^5R^6$, where $R^3$ to $R^6$ independently of one another stand for hydrogen or a C1 to C4 hydrocarbon group, monoglyceride sulfates and monoglyceride ether sulfates of the formula

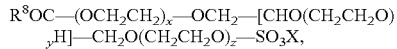

in which $R^8CO$ stands for a linear or branched acyl group having 6 to 22 carbon atoms, x, y and z in total for 0 or for numbers from 1 to 30, preferably 2 to 10, and X for an alkali or alkaline earth metal. Typical examples of monoglyceride (ether) sulfates suitable in the context of the invention are the reaction products of lauric acid monoglyceride, coconut fatty acid monoglyceride, palmitic acid monoglyceride, stearic acid monoglyceride, oleic acid monoglyceride, and tallow fatty acid monoglyceride, as well as the ethylene oxide adducts thereof with sulfur trioxide or chlorosulfonic acid in the form of their sodium salts. Preferably, monoglyceride sulfates are used in which $R^8CO$ stands for a linear acyl group having 8 to 18 carbon atoms, amide ether carboxylic acids, $R^1$—CO—$NR^2$—$CH_2CH_2$—O—$(CH_2CH_2O)_nCH_2COOM$, with $R^1$ as a straight-chain or branched alkyl or alkenyl group having a number of carbon atoms in the chain from 2 to 30, n stands for an integer from 1 to 20, and $R^2$ stands for hydrogen, a methyl, ethyl, propyl, isopropyl, n-butyl, t-butyl, or isobutyl group, and M stands for hydrogen or a metal such as an alkali metal, in particular sodium, potassium, lithium, alkaline earth metal, in particular magnesium, calcium, zinc, or an ammonium ion, such as $^+NR^3R^4R^5R^6$, with $R^3$ to $R^6$ independently of one another standing for hydrogen or a C1 to C4 hydrocarbon groups. Products of this type are obtainable, for example, from the company Chem-Y under the product name Akypo®, and acyl glutamates of the formula XOOC—CH2CH2CH(C(NH)OR)—COOX, in which RCO stands for a linear or branched acyl group having 6 to 22 carbon atoms and 0 and/or 1, 2, or 3 double bonds and X for hydrogen, an alkali and/or alkaline earth metal, ammonium, alkyl ammonium, alkanol ammonium, or glucammonium.

In a further embodiment, very particularly preferred is a method for reducing skin staining during the coloring of hair, comprising the following steps in the indicated sequence:

A1) applying a coloring agent (F) to the hair,
A2) allowing the coloring agent (F) to act for a time period from 30 seconds to 45 minutes,
B1) applying an undiluted cleaning agent (R) to skin areas that can come into contact with the coloring agent (F) when the latter is washed out,
C1) jointly (i.e., concurrently) washing out the coloring agent (F) and cleaning agent (R),
wherein
the coloring agent (F) includes at least one oxidation dye precursor and/or at least one direct dye and
the cleaning agent (R) at least one anionic surfactant from the group comprising $C_8$-$C_{30}$ alkane sulfonates, $C_8$-$C_{30}$ alkyl ether sulfonates, $C_8$-$C_{30}$ alkyl sulfates, and $C_8$-$C_{30}$ fatty alcohol ether sulfates.

The skilled artisan has long known that the pH of a hair coloring agent can have a massive influence on the intensity and shades of the coloring.

On the one hand, the extent of the swelling of the keratin material depends on the pH of the coloring agent. In this case, it applies in principle that the swelling of the hair is the greater, the more basic the agent applied to the hair. Greater swelling of the hair in turn promotes the diffusion of the dyes into the hair fibers. In particular, coloring agents that include neutral direct dyes (for example, nitro dyes) or cationic dyes (such as, for example, azo dyes with a quaternary ammonium group) normally produce a more intense color result when they are adjusted to a higher pH. Similar rules apply to skin staining as well; i.e., coloring agents that include neutral direct dyes (for example, nitro dyes) or cationic dyes (such as, for example, azo dyes with a quaternary ammonium group) also produce more intense skin staining when they are adjusted to a higher pH.

In contrast, for coloring with acid dyes, i.e., with dyes that carry at least one anionic charge in the form of a carboxylate or sulfonate group, an acid pH must be established to assure a sufficiently high color absorption. Thus, the color result achievable with acid dyes is normally intensified by lowering the pH.

It has emerged as very particularly advantageous in this regard to adapt the pH of the coloring agent (F) and the pH of the cleaning agent (R) to these rules and to one another.

If the coloring agent (F) includes, for example, a cationic direct dye, thus an especially intense color result on the hair could be achieved, if the coloring agent (F) was adjusted to a neutral, particularly preferably to an alkaline pH. It has now emerged in the subsequent use of the cleaning agent (R) that a cleaning agent adjusted to an acid pH reduces the coloring potential of the cationic dyes; i.e., the coloring agent (F) and cleaning agent (R), whose pH was reduced, mixed together during the washing out and the potential of the dyes for skin staining was reduced. Because this change in pH occurred only at the time of the washing out, the color result previously achieved on the hair was not affected by this.

If the coloring agent (F), on the other hand, includes an anionic direct dye, thus an especially intense color result on the hair could be achieved, if the coloring agent (F) was adjusted to an acid pH. It has now emerged in the subsequent use of the cleaning agent (R) that a cleaning agent adjusted to a neutral to alkaline pH reduces the coloring potential of the anionic dyes; i.e., the coloring agent (F) and cleaning agent (R), whose pH was increased, mixed together during the washing out and the potential of the dyes for skin staining was again reduced in a similar way. Because this pH change occurred only at the time of the washing out, the color result previously achieved on the hair was also not affected in this case.

In summary, it therefore emerged as very particularly preferable, if the pH of the cleaning agent (R) and the pH of the coloring agent (F) differ. The difference in the pH units in this case can be 1.5 pH units, preferably at least 2.0 pH units, more preferably at least 3.0 pH units, and very particularly preferably at least 4.0 pH units. A prerequisite for determining the pH here is that both the coloring agent (F) and the cleaning agent (R) include water.

In a further embodiment, explicitly very particularly preferred is a method for reducing the skin staining during the coloring of hair, which is characterized in that the coloring agent (F) includes water and
the cleaning agent (R) includes water and
the pH of the cleaning agent (R) differs by at least 1.5 pH units, preferably by at least 2.0 pH units, more preferably by at least 3.0 pH units, and very particularly preferably by at least 4.0 pH units from the pH of the coloring agent (F).

The pH can be measured, for example, with a glass electrode which is typically made in the form of a single-rod measuring chain. pH values of the present invention are pH values measured at a temperature of 22° C.

To carry out the method of the invention, in particular the explicitly very particularly preferred embodiment described last, the user employs a coloring agent (F) and a cleaning agent (R) in the above-described manner.

Very particularly preferably, in this case the coloring agent (F) and the cleaning agent (R) (i.e., the liquid gloves) are matched to one another in regard to their pH. It is particularly convenient for the user if this agent is provided to him/her in the form of a multicomponent packaging unit (kit of parts).

A second subject of the present invention therefore is a multicomponent packaging unit (kit of parts) for coloring hair with reduced skin staining, comprising, packaged separately from one another, an aqueous coloring agent (F) and
an aqueous cleaning agent (R), wherein
the coloring agent (F) includes at least one oxidation dye precursor and/or at least one direct dye and
the cleaning agent (R) includes at least one anionic surfactant, and
the pH of the cleaning agent (R) differs by at least 1.5 pH units, preferably by at least 2.0 pH units, more preferably by at least 3.0 pH units, and very particularly preferably by at least 4.0 pH units from the pH of the coloring agent (F).

The multicomponent packaging unit (kit of parts) of the invention for coloring hair with reduced skin staining comprises at least two components, a coloring agent (F) and a cleaning agent (R), that are produced separately (i.e., separately packaged).

The multicomponent packaging unit can comprise in addition also one or more other separately packaged components, for example, another component that includes an oxidizing agent, and/or another component that is a pretreatment agent.

Furthermore, the multicomponent packaging unit of the invention may include instructions for use, as well as a comb, an applicator, a dye brush, a spout, or a brush. The multicomponent packaging unit is to be used for coloring hair with reduced skin staining, without the user being instructed to use gloves. In a very particularly preferred embodiment, the multicomponent packaging unit of the invention therefore comprises no gloves.

In a very particularly preferred embodiment, the multicomponent packaging unit of the invention is characterized in that it includes optionally instructions for use and
optionally a comb, an applicator, a dye brush, a spout, or a brush and
no gloves.

As already disclosed in the description of the method of the invention, the skin can be stained especially greatly during use of anionic dyes (i.e., acid dyes). The use of the cleaning agent (R) according to the liquid gloves principle protects the skin in particular from the effects of acid dyes. For this reason, the coloring agent (F) of the multicomponent packaging unit of the invention preferably includes at least one anionic direct dye.

In a very particularly preferred embodiment, the method of the invention is characterized in that the coloring agent (F) includes at least one anionic direct dye.

In a very particularly preferred embodiment, the multicomponent packaging unit of the invention is characterized in that the coloring agent (F) includes at least one anionic direct dye.

For example, the representatives that were already disclosed in the description of the method of the invention can be selected as suitable acid dyes.

Furthermore, very particularly preferred is a multicomponent packaging unit (kit of parts) for coloring hair with reduced skin staining, comprising, separately packaged, an aqueous coloring agent (F) and
an aqueous cleaning agent (R), wherein
the coloring agent (F) includes at least one direct dye and
the cleaning agent (R) includes at least one anionic surfactant, and
the pH of the cleaning agent (R) differs by at least 1.5 pH units, preferably by at least 2.0 pH units, more preferably by at least 3.0 pH units, and very particularly preferably by at least 4.0 pH units from the pH of the coloring agent (F).

Furthermore, very particularly preferred is a multicomponent packaging unit (kit of parts) for coloring hair with reduced skin staining, comprising, separately packaged, an aqueous coloring agent (F) and
an aqueous cleaning agent (R), wherein
the coloring agent (F) includes at least one direct dye and
the cleaning agent (R) includes at least one anionic surfactant, and
the pH of the cleaning agent (R) differs by at least 3.0 pH units from the pH of the coloring agent (F).

Furthermore, very particularly preferred is a multicomponent packaging unit (kit of parts) for coloring hair with reduced skin staining, comprising, separately packaged, an aqueous coloring agent (F) and
an aqueous cleaning agent (R), wherein
the coloring agent (F) includes at least one direct dye and
the cleaning agent (R) includes at least one anionic surfactant, and
the pH of the cleaning agent (R) differs by at least 4.0 pH units from the pH of the coloring agent (F).

Furthermore, very particularly preferred is a multicomponent packaging unit (kit of parts) for coloring hair with reduced skin staining, comprising, separately packaged, an aqueous coloring agent (F) and
an aqueous cleaning agent (R), wherein
the coloring agent (F) includes at least one anionic direct dye and
the cleaning agent (R) includes at least one anionic surfactant, and the pH of the cleaning agent (R) differs by at least 3.0 pH units from the pH of the coloring agent (F).

Furthermore, very particularly preferred is a multicomponent packaging unit (kit of parts) for coloring hair with reduced skin staining, comprising, separately packaged,
- an aqueous coloring agent (F) and
- an aqueous cleaning agent (R), wherein
- the coloring agent (F) includes at least one anionic direct dye and
- the cleaning agent (R) includes at least one anionic surfactant, and
- the pH of the cleaning agent (R) differs by at least 4.0 pH units from the pH of the coloring agent (F).

As already described above, it has emerged as very particularly preferable, in particular if the coloring agent (F) includes at least one anionic direct dye, to raise the pH of the cleaning agent (R) in comparison with the pH of the coloring agent (F). Particularly preferably, the cleaning agent (R) has a pH that is higher by at least 1.5 pH units, preferably by at least 2.0 pH units, more preferably by at least 3.0 pH units, and very particularly preferably by at least 4.0 pH units than the pH of the coloring agent (F).

Example

The coloring agent (F) includes various acid dyes and was adjusted to a pH of 2.2.

Preferably, the cleaning agent (R) has a pH of at least 3.7, more preferably of at least 4.2, even more preferably of at least 5.2, and very particularly preferably of at least 6.2.

In a very especially preferred embodiment, the method of the invention is characterized in that the pH of the cleaning agent (R) is higher by at least 1.5 pH units, preferably by at least 2.0 pH units, more preferably by at least 3.0 pH units, and very particularly preferably by at least 4.0 pH units than the pH of the coloring agent (F).

In a very particularly preferred embodiment, the multicomponent packaging unit of the invention is characterized in that the pH of the cleaning agent (R) is higher by at least 1.5 pH units, preferably by at least 2.0 pH units, more preferably by at least 3.0 pH units, and very particularly preferably by at least 4.0 pH units than the pH of the coloring agent (F).

To achieve an especially good protective effect from the dyes, it has emerged as very particularly advantageous to use the coloring agent (F) and the cleaning agent (R) in a specific weight ratio to one another.

The higher the quantitative ratio of the cleaning agent (R) to the coloring agent (F), i.e., the higher the weight ratio (R)/(F), the greater the protective effect of the cleaning agent (R) in comparison with (F), because above all if the amount used of the cleaning agent (R) is sufficient, there is a complete and uninterrupted layer on the particular skin areas.

The quantitative ratio of (R)/(F) can be influenced by various factors. It is a possibility, for example, to use the coloring agent (F) in the form of a color foam. To obtain a color foam, the agent can be produced, for example, in the form of an aerosol.

An aerosol is a disperse system in which a solid or liquid is present very finely distributed in a gas. The aerosol is normally produced only during use with the aid of a suitable spray system by spraying of solutions, emulsions, or suspensions themselves, for which purpose, for example, spray cans can be used, in which a liquefied compressed gas serves as a propellant. When the pressure valve is opened, the propellant preparation mixture escapes through a fine nozzle; the propellant evaporates and leaves behind the finely distributed spray material as an aerosol or spray foam.

A coloring agent (F) present in foam form has a much lower density than a conventional coloring agent present in the form of a solution, gel, or emulsion.

If, for example, 4 g of coloring agent (F) is discharged by the propellant, thus the propellant greatly foams up the coloring agent. When propane/butane is used as the propellant, 4 g of the foam can have a volume of 150 to 200 mL. The corresponding foam density (unit g/L) is 26.7 g/L to 20.0 g/L.

A simple measurement of the foam density can occur, for example, by filling a container having a defined volume to a calibration mark with the color foam. Next, the amount of foam is weighed. The ratio of the foam weight to the foam volume, converted to 1000 mL, then produces the foam density.

In a very particularly preferred embodiment, the method of the invention is characterized in that the coloring agent (F) is applied to hair in the form of a foam with a foam density of 5 to 300 g/L, preferably of 10 to 200 g/L, more preferably of 15 to 100 g/L, and very particularly preferably of 20 to 80 g/L.

In a very particularly preferred embodiment, the multicomponent packaging unit of the invention is characterized in that the coloring agent (F) is applied to hair in the form of a foam with a foam density of 5 to 300 g/L, preferably of 10 to 200 g/L, more preferably of 15 to 100 g/L, and very particularly preferably of 20 to 80 g/L.

In a further very particularly preferred embodiment, the multicomponent packaging unit of the invention is characterized in that the coloring agent (F) is produced in the form of an aerosol.

The foam-type coloring agent (F) in the given volume has an especially low weight, so that in fact complete wetting of the hair areas to be colored is possible, but the coloring agent (F) amount, used in comparison with the cleaning agent (R), is relatively low (provided the cleaning agent (R) is not used in foam form).

It is very particularly preferred in this regard to use the coloring agent (F) in the form of the above-described foam, but to produce the cleaning agent (R) as a conventional shampoo, for example, in the form of a solution, gel, or emulsion. The density of these production forms in terms of magnitude is in the range of 800 to 1200 g/L.

In a very particularly preferred embodiment, the method of the invention is characterized in that the cleaning agent (R) has a density of 800 to 1200 g/L.

In a very particularly preferred embodiment, the multicomponent packaging unit of the invention is characterized in that the cleaning agent (R) has a density of 800 to 1200 g/L.

In the case of production in the form of an aerosol or color foam, the coloring agent (F) of the invention includes furthermore in addition at least one propellant. For example, dimethyl ether, propane, propene, n-butane, isobutane, isobutene, n-pentane, pentene, isopentane, and/or isopentene can be used as suitable propellants.

In a very particularly preferred embodiment, the method of the invention is characterized in that the coloring agent (F) includes one or more additional propellants selected from the group comprising dimethyl ether, propane, propene, n-butane, isobutane, isobutene, n-pentane, pentene, isopentane, and isopentene.

In a very particularly preferred embodiment, the multicomponent packaging unit of the invention is characterized in that the coloring agent (F) includes one or more additional propellants selected from the group comprising dimethyl ether, propane, propene, n-butane, isobutane, isobutene, n-pentane, pentene, isopentane, and isopentene.

Furthermore, it has emerged as preferable if the coloring agent (F) also includes the propellants (f) in specific amount ranges. In a preferred embodiment, the coloring agent (F) of the invention includes, based on the total weight of the propellant-containing composition (F), one or more additional propellants (f), therefore in a total amount of 1 to 10% by weight, preferably of 2 to 9% by weight, more preferably of 3 to 8% by weight, and particularly preferably of 4 to 7% by weight.

Furthermore, the quantitative ratio of (R)/(F) is simply also optimized in that the cleaning agent (R) in comparison with the coloring agent (F) is used in at least an equal amount, but preferably in excess. Particularly preferably, the coloring agent (F) and the cleaning agent (R) are used in a weight ratio (F)/(R) of 1:1 to 1:10, preferably of 1:1 to 1:5, more preferably of 1:2 to 1:5, and very particularly preferably of 1:3 to 1:5.

In a very particularly preferred embodiment, the method of the invention is characterized in that the coloring agent (F) and the cleaning agent (R) are used in a weight ratio (F)/(R) of 1:1 to 1:10, preferably of 1:1 to 1:5, more preferably of 1:2 to 1:5, and very particularly preferably of 1:3 to 1:5.

In a very particularly preferred embodiment, the multicomponent packaging unit of the invention is characterized in that the coloring agent (F) and the cleaning agent (R) are used in a weight ratio (F)/(R) of 1:1 to 1:10, preferably of 1:1 to 1:5, more preferably of 1:2 to 1:5, and very particularly preferably of 1:3 to 1:5.

When an excess of the cleaning agent (R) is used, a higher amount of the cleaning agent (R) is also consumed than of the coloring agent (F). Accordingly, in this embodiment of the multicomponent packaging unit, the provided amounts of both agents also differ. Accordingly, it is particularly preferred, if the multicomponent packaging unit includes the cleaning agent (R) in an amount that is greater by a factor of up to 10 than the amount of the provided coloring agent. The multicomponent packaging unit preferably includes the cleaning agent (R) and the coloring agent (F) in a weight ratio (F)/(R) of 1:1 to 1:10, preferably of 1:1 to 1:5, more preferably of 1:2 to 1:5, and very particularly preferably of 1:3 to 1:5.

Example

A multicomponent packaging unit includes
50 g of coloring agent (F) and
150 g of cleaning agent (R).

The multicomponent packaging unit includes the agents (F) and (R) in a weight ratio of 1:3.

In a very particularly preferred embodiment, the multicomponent packaging unit of the invention is characterized in that it includes the coloring agent (F) and the cleaning agent (R) in a weight ratio (F)/(R) of 1:1 to 1:10, preferably of 1:1 to 1:5, more preferably of 1:2 to 1:5, and very particularly preferably of 1:3 to 1:5.

The coloring agent (F) and the cleaning agent (R) are provided preferably as a liquid, in particular as an aqueous preparation.

At least one surface-active substance can be added in addition to the coloring agent (F), wherein such surface-active substances are called surfactants or emulsifiers depending on the field of application: They are preferably selected from anionic, zwitterionic, amphoteric, and nonionic surfactants and emulsifiers. The addition of at least one surfactant to stabilize the foam is advantageous in particular when the coloring agent (F) is produced in the form of a color foam.

The presence of at least one anionic surfactant is essential to the invention for the cleaning agent (R). The cleaning agent (R) can include, based on the total weight of the cleaning agent (R), one or more anionic surfactants in a total amount of 4.0% by weight to 25.0% by weight, preferably of 5.0 to 20% by weight, more preferably of 6.0 to 15% by weight, and particularly preferably of 7.0 to 15% by weight.

In a very particularly preferred embodiment, the method of the invention is characterized in that the cleaning agent (R) includes, based on the total weight of the cleaning agent (R), one or more anionic surfactants in a total amount of 4.0% by weight to 25.0% by weight, preferably of 5.0 to 20% by weight, more preferably of 6.0 to 15% by weight, and particularly preferably of 7.0 to 15% by weight.

In a very particularly preferred embodiment, the multicomponent packaging unit of the invention is characterized in that the cleaning agent (R) includes, based on the total weight of the cleaning agent (R), one or more anionic surfactants in a total amount of 4.0% by weight to 25.0% by weight, preferably of 5.0 to 20% by weight, more preferably of 6.0 to 15% by weight, and particularly preferably of 7.0 to 15% by weight.

To improve the protective effect of the cleaning agent (R) further, it can include additionally also one or more amphoteric and/or zwitterionic surfactants.

Preferred zwitterionic surfactants are betaines, N-alkyl-N,N-dimethylammonium glycinates, N-acylaminopropyl-N,N-dimethylammonium glycinates, and 2-alkyl-3-carboxymethyl-3-hydroxyethyl imidazolines. A preferred zwitterionic surfactant is known by the INCI name Cocamidopropyl Betaine.

Preferred amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids. Particularly preferred amphoteric surfactants are N-cocoalkyl aminopropionate, cocoacylaminoethyl aminopropionate, and $C_{12}$-$C_{18}$ acylsarcosine.

In a very particularly preferred embodiment, the method of the invention is characterized in that the cleaning agent (R) includes, based on the total weight of the cleaning agent (R), in addition one or more amphoteric and/or zwitterionic surfactants in a total amount of 1.5% by weight to 10.0% by weight, preferably of 2.0 to 8.0% by weight, and particularly preferably of 2.5 to 6.0% by weight.

In a very particularly preferred embodiment, the multicomponent packaging unit of the invention is characterized in that the cleaning agent (R) includes, based on the total weight of the cleaning agent (R), in addition one or more amphoteric and/or zwitterionic surfactants in a total amount of 1.5% by weight to 10.0% by weight, preferably of 2.0 to 8.0% by weight, and particularly preferably of 2.5 to 6.0% by weight.

Furthermore, the coloring agent (F) and/or the cleaning agent (R) can include in addition one or more nonionogenic surface-active substances. Preferred nonionic surfactants are alkyl polyglycosides and alkylene oxide adducts to fatty alcohols and fatty acids with in each case 2 to 30 mol of ethylene oxide per mole of fatty alcohol or fatty acid. Preparations with excellent properties are likewise obtained if they include fatty acid esters of ethoxylated glycerol as the nonionic surfactants.

The nonionic, zwitterionic, or amphoteric surfactants are used in proportions of 0.1 to 45% by weight, preferably 1 to 30% by weight, and very especially preferably of 1 to 15% by weight, based on the total amount of the particular agent.

It has also emerged as advantageous if the agents include at least one thickener. There are no basic restrictions with regard to these thickeners. Both organic and purely inorganic thickeners may be used.

Suitable thickeners are anionic, synthetic polymers; cationic, synthetic polymers; naturally occurring thickeners, such as nonionic guar gums, scleroglucan gums or xanthan gums, gum arabic, gum ghatti, karaya gum, tragacanth gum, carrageenan gum, agar-agar, locust bean flour, pectins, alginates, starch fractions, and derivatives such as amylose, amylopectin, and dextrins, as well as cellulose derivatives such as, for example, methylcellulose, carboxyalkylcelluloses, and hydroxyalkylcelluloses; nonionic, fully synthetic polymers such polyvinyl alcohol or polyvinylpyrrolidinone; as well as inorganic thickeners, in particular phyllosilicates such as, for example, bentonite, in particular smectites, such as montmorillonite or hectorite.

The coloring agent (F) of the invention and/or the cleaning agent (R) can also include anionic polymers thickeners. Suitable compounds are selected, for example, from crosslinked or non-crosslinked copolymers that include at least two different monomers from the group comprising acrylic acid, methacrylic acid, $C_1$-$C_6$ alkyl esters of acrylic acid, and/or $C_1$-$C_6$ alkyl esters of methacrylic acid. Particularly preferred anionic copolymers are copolymers of acrylic acid, methacrylic acid, or the $C_1$-$C_6$ alkyl esters thereof, which are marketed under the INCI name of Acrylates Copolymer. Preferred in particular is the combination of methacrylic acid and ethyl acrylate and optionally crosslinked, multifunctional monomers. A preferred commercial product for this is, for example, Aculyn® 33 or 33A, which is sold by the company Rohm & Haas.

Furthermore, the coloring agent (F) and/or the cleaning agent (R) can include one or more polymers from the group comprising Polyquaternium-1, Polyquaternium-2, Polyquaternium-3, Polyquaternium-4, Polyquaternium-5, Polyquaternium-6, Polyquaternium-7, Polyquaternium-8, Polyquaternium-9, Polyquaternium-10, Polyquaternium-11, Polyquaternium-14, Polyquaternium-16, Polyquaternium-17, Polyquaternium-18, Polyquaternium-22, Polyquaternium-24, Polyquaternium-27, Polyquaternium-28, Polyquaternium-32, Polyquaternium-33, Polyquaternium-37, Polyquaternium-39, Polyquaternium-44, Polyquaternium-46, Polyquaternium-53, Polyquaternium-55, Polyquaternium-64, Polyquaternium-67, Polyquaternium-68, Polyquaternium-69, and/or Polyquaternium-86.

In one embodiment, the coloring agent (F) and/or the cleaning agent (R) can also include one or more cationic surfactants. All conventional cationic surfactants, known to the skilled artisan, can be used as cationic surfactants according to the invention. These include:
 quaternary imidazoline compound. The formula Quimi-I illustrated hereafter shows the structure of these compounds.

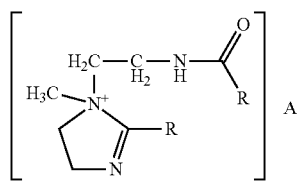

The R groups independently of one another each stand for a saturated or unsaturated, linear or branched hydrocarbon group with a chain length of 8 to 30 carbon atoms. The preferred compounds of the formula I include in each case the same hydrocarbon group for R. The chain length of the R groups is preferably 12 to 21 carbon atoms. Particularly inventive examples are obtainable, for example, under the INCI names: Quaternium-27, Quaternium-72, Quaternium-83, and Quaternium-91.

cationic surfactants according to the formula (Tkat-2),

R herein stands for a substituted or unsubstituted, branched or straight-chain alkyl or alkenyl group having 11 to 35 carbon atoms in the chain, X stands for —O— or —NR$^5$—, R$^1$ stands for an alkylene group having 2 to 6 C atoms, which may be unsubstituted or substituted, wherein in the case of a substitution, substitution with an —OH or —NH group is preferred, R$^2$, R$^3$, each independently of one another stand for an alkyl or hydroxyalkyl group having 1 up to 6 C atoms in the chain, wherein the chain can be straight or branched.

R$^5$ stands for hydrogen or a C1 to C6 straight-chain or branched alkyl or alkenyl group, which may also be substituted by a hydroxy group.

Compounds of one of the following structures are used with preference within this structure class:

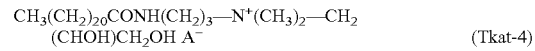

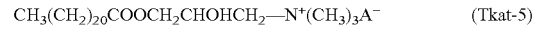

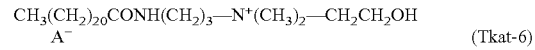

Examples of commercial products of this kind are Schercoquat BAS, Lexquat AMG-BEO, Akypoquat 131, or Incroquat Behenyl HE.

Esterquats according to the formula (Tkat1-2) are used.

Herein, the groups R1, R2, and R3 are each independent of one another and may be the same or different. The groups R1, R2, and R3 denote:
 a branched or unbranched alkyl group having 1 to 4 carbon atoms which can include at least one hydroxyl group, or
 a saturated or unsaturated, branched or unbranched or a cyclic saturated or unsaturated alkyl group having 6 to 30 carbon atoms which can include at least one hydroxyl group, or
 an aryl or alkaryl group, for example, phenyl or benzene,
 the group (-A-R4), with the proviso that at most 2 of the groups R1, R2, or R3 can stand for this group:
The group -(A-R4) is included at least 1 to 3 times.

Herein A stands for:
1) —(CH2)n- with n=1 to 20, preferably n=1 to 10, and particularly preferably n=1 to 5, or
2) —(CH2-CHR5-O)n- with n=1 to 200, preferably 1 to 100, particularly preferably 1 to 50, and especially preferably 1 to 20 with R5 having the meaning of hydrogen, methyl, or ethyl, and R4 stands for:
1) R6-O—CO—, where R6 is a saturated or unsaturated, branched or unbranched or a cyclic saturated or unsaturated alkyl group having 6 to 30 carbon atoms, which can include at least one hydroxy group, and which optionally can be oxethylated furthermore with 1 to 100 ethylene oxide units and/or 1 to 100 propylene oxide units, or
2) R7-O—CO—, where R7 is a saturated or unsaturated, branched or unbranched or a cyclic saturated or unsaturated alkyl group having 6 to 30 carbon atoms, which can include at least one hydroxy group, and which optionally can be oxethylated furthermore with 1 to 100 ethylene oxide units and/or 1 to 100 propylene oxide units, and Q stands for a physiologically acceptable organic or inorganic anion.

Such products are marketed, for example, under the trademarks Rewoquat®, Stepantex®, Dehyquart®, and Armocare®. The products Armocare® VGH-70, a N,N-bis(2-palmitoyloxyethyl)dimethylammonium chloride, as well as Dehyquart® F-75, Dehyquart® C-4046, Dehyquart® L80, Dehyquart® F-30, Dehyquart® AU-35, Rewoquat® WE18, Rewoquat® WE38 DPG, and Stepantex® VS 90 are examples of such esterquats.

Other compounds of the formula (Tkat1-2) that are particularly preferred according to the invention include the cationic betaine esters of formula (Tkat1-2.1).

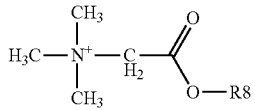
(Tkat1-2.1)

R8 corresponds in its meaning to R7.

monoalkyltrimethylammonium salts with a chain length of the alkyl group of 16 to 24 carbon atoms according to the formula (Tkat1-1),

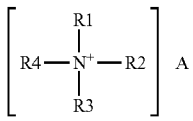
(Tkat1-1)

in which R1, R2, and R3 stand for a methyl group in each case and R4 stands for a saturated, branched or unbranched alkyl group with a chain length of 16 to 24 carbon atoms. Examples of compounds of the formula (Tkat1-1) are cetyltrimethylammonium chloride, cetyltrimethylammonium bromide, cetyltrimethylammonium methosulfate, stearyltrimethylammonium chloride, behenyltrimethylammonium chloride, behenyltrimethylammonium bromide, and behenyltrimethylammonium methosulfate.

amines and/or cationized amines, in particular an amidoamine and/or a cationized amidoamine with the following structural formulas:

$$R^1\text{—NH—}(CH_2)_n\text{—}NR^2R^3 \quad \text{(Tkat7) and/or}$$

$$R^1\text{—NH—}(CH_2)_n\text{—}NR^2R^3R^4 \quad \text{(Tkat8)}$$

where R1 denotes an acyl or alkyl group having 6 to 30 C atoms, which can be branched or unbranched, saturated or unsaturated, and wherein the acyl group and/or alkyl group can include at least one OH group, and R2, R3, and R4 in each case independently of one another denote hydrogen or an alkyl group having 1 to 4 C atoms, which may be identical or different, saturated or unsaturated, and X– an anion, and
n an integer between 1 and 10.

A composition is preferred in which the amine and/or the quaternized amine according to the general formulas (Tkat7) and/or (Tkat8) are an amidoamine and/or a quaternized amidoamine in which R1 denotes a branched or unbranched, saturated or unsaturated acyl group having 6 to 30 C atoms, which can include at least one OH group. A fatty acid group from oils and waxes, in particular from natural oils and waxes, is preferred here. Suitable examples include lanolin, beeswax, or candelilla wax. Also preferred are amidoamines and/or quaternized amidoamines in which R2, R3, and/or R4 in the formulas (Tkat7) and/or (Tkat8) denote a group according to the general formula $CH_2CH_2OR5$, where R5 can have the meaning of alkyl groups having 1 to 4 carbon atoms, hydroxyethyl, or hydrogen. The preferred value of n in the general formulas (Tkat7) and/or (Tkat 8) is an integer between 2 and 5. Preferred furthermore are amidoamines and/or quaternized amidoamines of the general formulas (Tkat7) and/or (Tkat8), in which the anion $X^-$ is a halide ion or a compound of the general formula $RSO_3^-$, where R has the meaning of saturated or unsaturated alkyl groups having 1 to 4 carbon atoms. The alkyl group having 1 to 4 carbon atoms of R2, R3, and R4 and/or the alkyl group having 1 to 4 carbon atoms of $RSO_3^-$ in the general formula (Tkat7) and/or (Tkat8) can include at least one hydroxyl group. The alkyl amidoamines can be present as is and can be converted into a quaternary compound in the composition by protonation in a suitably acid solution. Cationic alkyl amidoamines are preferred according to the invention.

As amidoamines to be used according to the invention, which optionally may be quaternized, for example, the following can be considered as amidoamines: Witcamine® 100 (Witco, INCI name: Cocamidopropyl Dimethylamine), Incromine® BB (Croda, INCI name: Behenamidopropyl Dimethylamine), Mackine® 401 (McIntyre, INCI name: Isostearylamidopropyl Dimethylamine) and other Mackine types, Adogen® S18V (Witco, INCI name: Stearylamidopropyl Dimethylamine), and as permanently cationic aminoamines: Rewoquat® RTM 50 (Witco Surfactants GmbH, INCI name: Ricinoleamidopropyltrimonium Methosulfate), Empigen® CSC (Albright&Wilson, INCI name: Cocamidopropyltrimonium Chloride), Swanol® Lanoquat DES-50 (Nikko, INCI name: Quaternium-33), and Rewoquat® UTM 50 (Witco Surfactants GmbH, Undecyleneamidopropyltrimonium Methosulfate).

The anion of all above-described cationic compounds is selected from physiologically acceptable anions. Named by way of example are the halide ions, fluoride, chloride, bromide, sulfates of the general formula $RSO_3^-$, where R has the meaning of saturated or unsaturated alkyl groups having 1 to 4 carbon atoms, or anionic groups of organic acids such as maleate, fumarate, oxalate, tartrate, citrate, lactate, or acetate.

Cationic imidazolines, esterquats, cationic surfactants according to the formula (Tkat-2) and amines and/or cationized amines, in particular amidoamines and/or cationized amidoamines are used with preference.

The aforesaid cationic surfactants can be used individually or in any combinations with one another, wherein they are included in amounts between 0.01 to 20% by weight, preferably in amounts of 0.01 to 10% by weight, and very particularly preferably in amounts of 0.1 to 7.5% by weight. The very best results in this case are obtained with amounts of 0.1 to 5% by weight, in each case based on the total composition of the particular agent.

The surfactants are used in a total amount of the surfactants in amounts of 0.05 to 45% by weight, preferably 0.1 to 30% by weight, and very particularly preferably of 0.5 to 25% by weight, based on the total agent used according to the invention.

The cationic surfactants are used in amounts of 0.1 to 45% by weight, preferably 1 to 30% by weight, and very especially preferably of 1 to 15% by weight, based in each case on the total amount of the particular agent.

Further, the coloring agent (F) and/or the cleaning agent (R) include other active substances, auxiliary substances, and additives, such as, for example, nonionic polymers such as, for example, vinylpyrrolidinone/vinyl acrylate copolymers, polyvinylpyrrolidinone, vinylpyrrolidinone/vinyl acetate copolymers, polyethylene glycols, and polysiloxanes; additional silicones such as volatile or nonvolatile, straight-chain, branched or cyclic, crosslinked or noncrosslinked polyalkylsiloxanes (such as dimethicones or cyclomethicones), polyarylsiloxanes and/or polyalkylarylsiloxanes, particularly polysiloxanes with organofunctional groups, such as substituted or unsubstituted amines (amodimethicones), carboxy, alkoxy, and/or hydroxyl groups (dimethicone copolyols), linear polysiloxanes A)-polyoxyalkylene B) block copolymers, grafted silicone polymers; cationic polymers such as quaternized cellulose ethers, polysiloxanes with quaternary groups, dimethyldiallylammonium chloride polymers, acrylamide-dimethyldiallylammonium chloride copolymers, dimethylaminoethylmethacrylate-vinylpyrrolidinone copolymers quaternized with diethyl sulfate, vinylpyrrolidinone-imidazolinium-methochloride copolymers, and quaternized polyvinyl alcohol; zwitterionic and amphoteric polymers; anionic polymers such as, for example, polyacrylic acids or crosslinked polyacrylic acids; structurants such as glucose, maleic acid, and lactic acid, hair-conditioning compounds such as phospholipids, for example, lecithin and kephalins; perfume oils, dimethyl isosorbide, and cyclodextrins; fiber-structure-improving active substances, particularly mono-, di-, and oligosaccharides such as, for example, glucose, galactose, fructose, fruit sugar, and lactose; dyes for coloring the agent; antidandruff agents such as piroctone olamine, zinc omadine, and climbazole; amino acids and oligopeptides; protein hydrolysates with an animal and/or vegetable base, and in the form of their fatty acid condensation products or optionally anionically or cationically modified derivatives; vegetable oils; light stabilizers and UV blockers; active substances such as panthenol, pantothenic acid, pantolactone, allantoin, pyrrolidinone carboxylic acids, and salts thereof, as well as bisabolol; polyphenols, particularly hydroxycinnamic acids, 6,7-dihydroxycoumarins, hydroxybenzoic acids, catechins, tannins, leucoanthocyanidins, anthocyanidins, flavanones, flavones, and flavonols; ceramides or pseudoceramides; vitamins, provitamins, and vitamin precursors; plant extracts; fats and waxes such as fatty alcohols, beeswax, montan wax, and paraffins; swelling and penetration agents such as glycerol, propylene glycol monoethyl ether, carbonates, hydrogen carbonates, guanidines, ureas, and primary, secondary, and tertiary phosphates; opacifiers such as latex, styrene/PVP and styrene/acrylamide copolymers; pearlescent agents such as ethylene glycol mono- and distearate and PEG-3 distearate; pigments and propellants such as propane-butane mixtures, $N_2O$, dimethyl ether, $CO_2$, and air.

The selection of these additional substances is made by the skilled artisan according to the desired properties of the agents. In regard to other facultative components and the employed amounts of said components, reference is made expressly to relevant handbooks known to the skilled artisan. The additional active and auxiliary substances are used in the agents of the invention preferably in each case in amounts of 0.0001 to 25% by weight, in particular of 0.0005 to 15% by weight, based on the total weight of the particular agent.

The production of the coloring agent (F) of the invention in the form of an aerosol is explicitly very particularly preferable. In the context of this embodiment, the coloring agent (F) is packaged in a pressurized aerosol container, the pressurized aerosol container having an aerosol dispensing device with a spray valve.

Vessels made of metal (aluminum, tin plate, tin), protected or non-splintering plastic or of glass that is externally coated with plastic may be used as compressed-gas containers; pressure resistance and breaking strength, corrosion resistance, ease of filling, as well as aesthetic aspects, handling, printability, etc., play a role in their selection. Special protective interior coatings assure corrosion resistance against the preparation included in the pressurized aerosol container.

It is especially advantageous, if the internal pressure of the pressurized aerosol container is at least 1.8 bar, in particular at least 2.5 bar.

The pressurized aerosol container containing the coloring agent (F) comprises furthermore an aerosol dispensing device, which has a spray valve to dispense the aerosol. In a preferred embodiment of the invention, the spray valve has a valve disc covered with a coating or a polymeric plastic A, and a flexible element of this kind with a reset function, which after the operation ends resets the valve to the closed position (=neutral position of the valve). Corresponding cosmetic products in which the aerosol dispensing device comprises a valve, which has a valve cone and/or a flexible element with a reset function and is/are covered with a coating or a polymeric plastic A, are preferred according to the invention.

In another preferred embodiment of the invention, the spray valve has a flexible element with a reset function and/or a valve disc made of at least one plastic B, preferably an elastomeric plastic. Here as well, cosmetic products of the invention in which the valve has a flexible element with a reset function and/or a valve cone made of at least one plastic B, are preferred, preferred plastics B being elastomeric plastics. Particularly preferred elastomeric plastics are selected from Buna, particularly Buna N, Buna 421, Buna 1602, and Buna KA 6712, neoprene, butyl, and chlorobutyl.

In another preferred embodiment of the invention, the flexible element with a reset function can be formed as a spiral spring or helical compression spring. In another preferred embodiment of the invention, the flexible element of the valve with the reset function can be formed integrally with the valve cone and have flexible legs. This spring can be made of metal or plastic.

In a particularly preferred embodiment of the invention, the valve cone and the flexible element are formed with a reset function. Particularly preferred in this case is valve type Ariane M, obtainable from the company Seaquist Perfect, in which the flexible element is formed with a reset function in the form of four elastic legs integrally with the valve cone.

All spray valves used according to the invention preferably have an internally coated valve disc, the coating and valve material being compatible with one another. If aluminum valves are used according to the invention, thus the valve discs thereof can be coated on the inside, e.g., with a Micoflex coating. If tin plate valves are used according to the invention, thus the valve discs thereof can be coated on the inside, e.g., with PET (polyethylene terephthalate). The employed containers, which can be made, e.g., of tin plate or aluminum, aluminum containers being preferred according to the invention, must also be painted or coated on the inside because of the corrosivity of the water-in-oil emulsions, used as taught by the invention. A protective interior coating preferred according to the invention is an epoxy phenolic coating, as can be obtained, among others, under the name Hoba 7407 P.

Very particularly preferably, the valve is a valve of the type Aptar ARM-4.00-1-0, 32-8, 70 Green—AR Housing—Valve-AHT-0.60-0.00-PA-Natural.

The statements made about the agents of the invention apply mutatis mutandis in regard to other preferred embodiments of the cosmetic multicomponent packaging unit of the invention.

Examples

1. Formulations

The following dyes (F) were produced (all quantities are given in percent by weight)

| Dye (F) | (F1) | (F2) | (F3) |
|---|---|---|---|
| Cocoglucoside (nonionic surfactant) | 1.5 | 1.5 | 1.5 |
| Potassium dihydrogen phosphate (KH$_2$PO$_4$) | 3.0 | 3.0 | 3.0 |
| Phosphoric acid (H$_3$PO$_4$) | To pH 2.2 | To pH 2.2 | To pH 2.2 |
| Phenoxyethanol | 0.81 | 0.81 | 0.81 |
| Xanthan | 1.0 | 1.0 | 1.0 |
| Benzyl alcohol | 9.4 | 9.4 | 9.4 |
| Acid Black No. 1 (acid dye) | 0.064 | 0.20 | 0.40 |
| Acid Violet 43 (acid dye) | 0.064 | 0.10 | 0.30 |
| Food Yellow 13 (acid dye) | 0.08 | 0.10 | 0.10 |
| Acid Red 52 (acid dye) | 0.08 | 0.30 | 0.5 |
| Acid Orange 7 (acid dye) | 0.24 | 0.50 | 0.5 |
| Perfume | 0.5 | 0.5 | 0.5 |
| Water | To 100 | To 100 | To 100 |

The following coloring foams (FS) were produced from the coloring agents (F1) to (F3).

| Coloring agent (F) | (FS1) | (FS2) | (FS3) |
|---|---|---|---|
| Coloring agent (F) | 90 | 90 | 90 |
| Propane/butane | 10 | 10 | 10 |

The following cleaning agents (R) were produced

| | Cleaning agents (R) |
|---|---|
| Natrium laureth sulfate (C12-C14 fatty alcohol sulfate with 2 EO) (anionic surfactant) | 8.5 |
| NaOH | 0.05 |
| Citric acid | To pH 5.4 |
| Disodium cocoamphodiacetate (amphoteric surfactant) | 2.0 |
| Sodium benzoate | 0.5 |
| D-Panthenol | 0.15 |
| Glycol distearate | 1.2 |
| Glycerol | 0.3 |
| Laureth-4 | 0.2 |
| Glycine | 0.2 |
| PEG-40 Hydrogenated Castor Oil | 0.1 |
| PEG-7 Glyceryl Cocoate | 0.3 |
| Hydrogenated Castor Oil | 0.1 |
| Cocamit MEo (Coconut fatty acid monoethanolamide) | 0.5 |
| Polyquaternium-10 | 0.08 |
| Cocoamidopropyl betaine (zwitterionic surfactant) | 1.48 |
| Sodium chloride | 1.0 |
| Water | to 100 |

2. Applications

Five subjects in each case with about 30% gray hair treated their hair according to the following process. None of the subjects wore gloves.

| (V) | (E) |
|---|---|
| 4 g of the color foam (F3) was applied in batches with the aid of a comb to the gray areas of the hair. | 4 g of the color foam (F3) was applied in batches with the aid of a comb to the gray areas of the hair. |
| — | 16 g of the cleaning agent (R) was distributed uniformly on the hands |
| The color foam (F3) was washed out under flowing water. The hair was then worked on with the hands. | Color foam (F3) and cleaning agent (R) were washed out jointly (concurrently) under flowing water. In so doing, the hair was worked on with the hands. |
| After the washing out, 16 g of the cleaning agent (R) was applied to the hair, distributed, and washed out again. | — |

Thereafter the skin staining on the hands of the subject was evaluated visually. An average was formed from the individual values.

| | (V) | (E) |
|---|---|---|
| Skin staining | 4-5 | 1-2 |

1 = very slight skin staining
5 = very great skin staining

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for reducing skin staining during the coloring of hair, comprising the following steps in the indicated sequence:
   A1) applying a coloring agent (F) to the hair,
   A2) allowing the coloring agent (F) to act for a time period from 30 seconds to 45 minutes on the hair,
   B1) applying an undiluted cleaning agent (R) to skin areas that can come into contact with the coloring agent (F) when the coloring agent (F) is washed out from the hair in step C1, and
   C1) jointly washing out the coloring agent (F) and cleaning agent (R),
   wherein
   the coloring agent (F) includes at least one oxidation dye precursor and/or at least one direct dye and
   the cleaning agent (R) includes at least one anionic surfactant.

2. The method according to claim 1, wherein the step A1) comprises applying the coloring agent (F) to the hair using a comb, an applicator, a dye brush, a spout, or a brush.

3. The method according to claim 1, wherein the step A2) comprises allowing the coloring agent (F) to act for a time period of 30 seconds to 5 minutes.

4. The method according to claim 1, wherein the step B1) comprises applying the undiluted cleaning agent (R) to the hands, ears, nape, forehead area, and/or skin areas adjacent to the hairline.

5. The method according to claim 1, wherein the step C1) comprises i.e., concurrently washing out the coloring agent (F) and cleaning agent (R) without the use of gloves.

6. The method according to claim 1, wherein
   the coloring agent (F) includes water,
   the cleaning agent (R) includes water, and
   the pH of the cleaning agent (R) differs by at least 1.5 pH units from the pH of the coloring agent (F).

7. The method according to claim 1, wherein the coloring agent (F) includes at least one anionic direct dye.

8. The method according to claim 1, wherein the pH of the cleaning agent (R) is higher by at least 1.5 pH units than the pH of the coloring agent (F).

9. The method according to claim 1, wherein the coloring agent (F) is applied to hair in the form of a foam with a foam density of 5 to 300 g/L.

10. The method according to claim 1, wherein the coloring agent (F) includes one or more propellants selected from the group consisting of dimethyl ether, propane, propene, n-butane, isobutane, isobutene, n-pentane, pentene, isopentane, and isopentene.

11. The method according to claim 1, wherein the coloring agent (F) and the cleaning agent (R) are used in a weight ratio (F)/(R) of 1:1 to 1:10.

12. The method according to claim 1, wherein the cleaning agent (R) includes, based on the total weight of the cleaning agent (R), one or more anionic surfactants in a total amount of 4.0% by weight to 25.0% by weight.

13. The method according to claim 12, wherein the cleaning agent (R) further includes, based on the total weight of the cleaning agent (R), one or more amphoteric and/or zwitterionic surfactants in a total amount of 1.5% by weight to 10.0% by weight.

* * * * *